United States Patent [19]
Kim et al.

[11] Patent Number: 5,679,559
[45] Date of Patent: Oct. 21, 1997

[54] CATIONIC POLYMER AND LIPOPROTEIN-CONTAINING SYSTEM FOR GENE DELIVERY

[75] Inventors: Jin-Seok Kim, Salt Lake City, Utah; Atsushi Maruyama, Yokohama; Toshihiro Akaike, Tokyo, both of Japan; Sung Wan Kim, Salt Lake City, Utah

[73] Assignee: University of Utah Research Foundation, Salt Lake City, Utah

[21] Appl. No.: 675,120

[22] Filed: Jul. 3, 1996

[51] Int. Cl.$^6$ ............................ C12N 15/64; C12N 15/88
[52] U.S. Cl. ............................ 435/172.3; 428/402.2; 530/359; 536/23.1
[58] Field of Search ............... 435/6, 172.3; 530/359; 536/23.1; 428/402.2; 514/44

[56] References Cited

U.S. PATENT DOCUMENTS 5,354,844  10/1994  Beug et al. .................... 530/345

*Primary Examiner*—James Ketter
*Attorney, Agent, or Firm*—Thorpe North & Western, L.L.P.

[57] ABSTRACT

A composition for delivery of a selected nucleic acid into a targeted host cell comprises a complex of a hydrophobized, positively charged, biocompatible polymer; a lipoprotein; and a selected nucleic acid. Hydrophobic and electrostatic interactions between the components provide for the formation of the condensed DNA-containing complex. Preferred embodiments of the complex have a slightly positive surface charge and an average diameter of about 200 nm. Plasmids and oligonucleotides can be efficiently delivered with such compositions. A method of delivering a selected nucleic acid to a host cell is also disclosed.

32 Claims, 4 Drawing Sheets

CATIONIC POLYMER AND LIPOPROTEIN-CONTAINING SYSTEM FOR GENE DELIVERY

BACKGROUND OF THE INVENTION

This invention relates to a system for delivering exogenous nucleic acid into a cell. More particularly, the invention relates to a delivery system, comprising a selected nucleic acid; a hydrophobized, positively-charged, biodegradable polymer; and a lipoprotein, for inserting the selected nucleic acid into a target cell.

Although human gene therapy shows great promise, its clinical efficacy has not yet been definitely established. R. Mulligan, 260 Science 926 (1993); R. M. Blease et al., 270 Science 475 (1995); I. M. Verma, 1 Mol. Med. 2 (1994); T. Friedmann, 1 Gene Ther. 217 (1994). Major difficulties lie in the lack of efficient and safe delivery systems for introducing genes into target cells. Until now, the majority of human gene therapy protocols have used gene delivery systems consisting of modified retroviruses or adenoviruses. A. Gitman et al., 82 Proc. Nat'l Acad. Sci. USA 7309 (1985); E. Gilboa et al., 4 Biotechniques 504 (1986). Retroviral vectors, in particular, have been successfully used for introducing new genes into the genomes of actively dividing cells such that stable transformants are obtained. D. G. Miller et al., 10 Mol. Cell Biol. 4239 (1990). This method of inserting a gene into the host cell's genome, however, is a random process, and its long-term risks due to the possibility of inserted genes combining with endogenous viruses or activation of oncogenes are a major concern. Such concerns have discouraged the use of such vectors in human gene therapy. D. G. Miller et al., 10 Mol. Cell Biol. 4239 (1990).

On the other hand, non-viral gene delivery systems, such as cationic liposomes, H. M. Temin, 1 Human Gene Therapy 111 (1990), or poly-L-lysine (PLL), G. Y. Wu & C. H. Wu, 263 J. Biol. Chem. 14621 (1988); E. Wagner et al., 87 Proc. Nat'l Acad. Sci. USA 3410 (1990); P. Felgner et al., 84 Proc. Nat'l Acad. Sci. USA 7314 (1987); H. Farhood et al., 1111 Biochim. Biophys. Acta 239 (1992), have drawbacks of low transfection efficiency or causing precipitation, even though they seem to be safe for human clinical use. N. H. Caplen et al., 1 Nature Medicine 1 (1995). Modified versions of poly(L-lysine) have been successfully exploited in various ways for improving delivery and expression of transfected genes, most notably for ligand conjugation for tissue targeting, D. T. Ciriel et al., 3 Human Gene Therapy 147 (1992); E. Wagner et al., 89 Proc. Nat'l Acad. Sci. USA 89 6099 (1992), and lipophilic poly(L-lysine), X. Zhou et al., 1065 Biochim. Biophys. Acta 8 (1991). Synthetic delivery systems also elicit fewer immunological complications with large scale or repeated use. P. L. Felgner, 5 Adv. Drug. Deliv. 163 (1990); J. P. Behr, 26 Acc. Chem. Res. 274 (1993); M. Cotten a E. Wagner, 4 Curr. Opin. Biotech. 705 (1993); J. P. Behr, 5 Bioconjugate Chem. 382 (1994).

In view of the foregoing, it will be appreciated that development of a gene delivery system that is both safe and efficient would be a significant advancement in the art.

BRIEF SUMMARY OF THE INVENTION

It is an object of the present invention to provide a composition and method for delivering a selected nucleic acid into a target cell.

It is also an object of the invention to provide a composition and method for gene delivery that are safe and efficient.

It is another object of the invention to provide an efficient, non-viral composition and method of use thereof for delivering exogenous DNA or RNA to a target cell.

These and other objects are achieved by providing a composition for delivery of a selected nucleic acid into a targeted host cell comprising a complex comprising an effective amount of a hydrophobized, positively charged, biocompatible polymer; an effective amount of a lipoprotein; and an effective amount of the selected nucleic acid. The hydrophobized polymer comprises a positively charged biocompatible polymer covalently coupled to a hydrophobic carbon chain moiety. A preferred positively charged biocompatible polymer is poly(L-lysine). The hydrophobic carbon chain moiety is preferably a member selected from the group consisting of saturated and unsaturated, straight-chains of $C_{14}$ to $C_{18}$, more preferably a stearyl group. The lipoprotein is preferably a member selected from the group consisting of low density lipoprotein, high density lipoprotein, and very low density lipoprotein. The selected nucleic acid is preferably a plasmid or a synthetic oligonucleotide. For a plasmid-containing complex, a weight ratio of 1:1:1 for hydrophobized polymer:lipoprotein:plasmid is especially preferred. For an oligonucleotide-containing complex, a weight ratio of 1:1:0.001–0.05 for hydrophobized polymer:lipoprotein:oligonucleotide is especially preferred. The composition preferably has a surface charge in the range of about 2–15 mV, and more preferably about +5 mV. A preferred average diameter of the composition is in the range of about 200 to 400 nm, and more preferably about 200 to 300 nm.

A method of transforming a cell in vitro with a selected nucleic acid comprises the steps of:

(a) providing a composition comprising a complex comprising an effective amount of a hydrophobized, positively charged, biocompatible polymer; an effective amount of a lipoprotein; and an effective amount of the selected nucleic acid.

(b) contacting the cell with an effective amount of the composition such that the cell internalizes the selected nucleic acid; and (c) culturing the cell with the internalized selected nucleic acid under conditions favorable for growth thereof.

DETAILED DESCRIPTION

Figure 1:
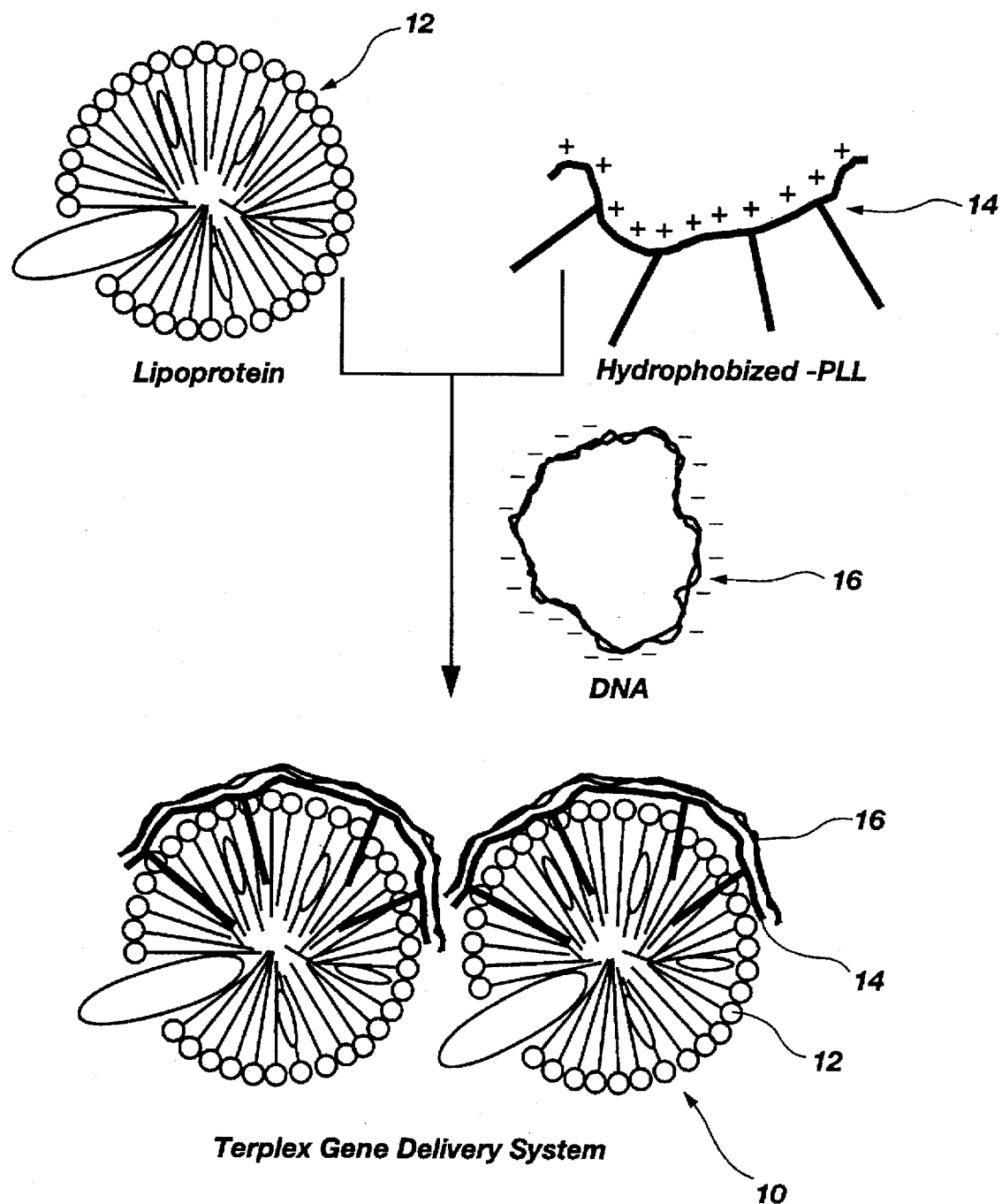
FIG. 1 shows a schematic representation of a lipoprotein component; a hydrophobized, positively-charged, biocompatible polymer; a nucleic acid molecule; and a complex thereof according to the present invention.

Before the present composition and method for delivery of exogenous nucleic acid to a targeted cell are disclosed and described, it is to be understood that this invention is not limited to the particular configurations, process steps, and materials disclosed herein as such configurations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

It must be noted that, as used in this specification and the appended claims, the singular forms "a," "an," and "the" include plural referents unless the context clearly dictates otherwise. Thus, for example, reference to a complex containing "a polymer" includes a mixture of two or more such polymers, reference to "a lipoprotein" includes reference to one or more of such lipoproteins, and reference to "a plasmid" includes reference to two or more of such plasmids.

In describing and claiming the present invention, the following terminology will be used in accordance with the definitions set out below.

As used herein, "effective amount" means an amount of a hydrophobized, positively charged, biocompatible polymer that, when complexed with a lipoprotein and a selected nucleic acid, is sufficient to provide a selected efficiency of delivery of the nucleic acid into a selected mammalian cell with an acceptable level of cytotoxicity. An effective amount of lipoprotein is an amount, when complexed with a selected nucleic acid and a hydrophobized polymer, sufficient to provide a selected efficiency of delivery of the selected nucleic acid into a selected mammalian cell with an acceptable level of cytotoxicity. Similarly, an effective amount of a selected nucleic acid is an amount, when complexed with a hydrophobized polymer and a lipoprotein, sufficient to provide a selected efficiency of delivery of the nucleic acid into a selected mammalian cell with an acceptable level of cytotoxicity. Such effective amounts of the hydrophobized polymer, lipoprotein, and nucleic acid can vary somewhat depending, for example, on the type of cell used, the nature of the nucleic acid, and the growth conditions of the cell. Such effective amounts can be routinely determined by a person skilled in the art without undue experimentation by following the guidelines set forth herein.

As used herein, "hydrophobized polymer" means a positively charged, biocompatible polymer that is modified by covalent bonding to a hydrophobic carbon chain. The positively charged, biocompatible polymer is preferable poly(L-lysine), poly(D-lysine), or polyarginine, and more preferably is poly(L-lysine). The molecular weight of the positively charged, biocompatible polymer is preferably in the range of about 500 to 50,000. The hydrophobic carbon chain is preferably a saturated or unsaturated straight chain of 14 to 18 carbon atoms. An especially preferred hydrophobic carbon chain is a stearyl group.

As used herein, "biocompatible" means compatible with growth of a cell that is to be or has been transformed with the present composition. Thus, biocompatible polymers are non-toxic to such cells and are preferably biodegradable.

As used herein, "lipoprotein" means a conjugate comprising a protein portion and a lipid portion. Preferred lipoproteins include the classes of lipoproteins known in the art as low density lipoprotein (LDL), high density lipoprotein (HDL), and very low density lipoprotein (VLDL). LDL and HDL are especially preferred. Without being bound by theory, it is believed that the presently claimed composition is effective in delivering a selected nucleic acid into a selected cell by endocytosis mediated by, for example, an LDL or HDL receptor on the surface of the selected cell. Efficiency of delivery can be improved by matching a cell having a high number of selected receptors on the surface thereof with a selected lipoprotein. For example, efficiency of delivery is improved by matching a cell having a high number of LDL receptors with a complex comprising LDL as the lipoprotein.

As used herein, "conditions favorable for growth" and similar terms mean conditions of temperature, pH, aerobic environment, presence of carbon source, presence of energy source, and the like that permit growth of selected mammalian cells.

FIG. 1 shows a schematic representation of a gene delivery composition 10 according to the present invention. The composition 10 is a complex of a lipoprotein component 12; a hydrophobized, positively-charged, biocompatible polymer 14; and a nucleic acid molecule 16. Hydrophobic interactions between the lipoprotein and the polymer enable the formation of a non-precipitating complex having a wide range of concentrations of the polymer. Such hydrophobic interactions involve the lipid portions of the lipoprotein and the hydrophobized polymer, respectively. Electrostatic interactions between the positively-charged polymer and the negatively-charged nucleic acid molecule allow formation of a condensed DNA-containing complex. Such electrostatic interactions involve the positively-charged portions of the positively-charged, hydrophobized polymer and the negatively-charged portions, predominantly the phosphodiester backbone, of the nucleic acid. It has been discovered that the balance between these two interactions is critical to optimizing efficiency of delivery, such that the net hydrophobicity and the surface charge of the complex should be carefully controlled. This balance will be discussed in more detail below.

EXAMPLE 1

Stearyl-PLL was synthesized by N-alkylation of poly(L-lysine) (MW 50,000) with stearyl bromide according to the following formula:

where R is a lysine residue exclusive of the α-amino group, R' is a stearyl group, and X is a halogen, e.g. R. T. Morrison & R. N. Boyd, Organic Chemistry 742 (3d ed. 1973). The degree of substitution in poly(L-lysine) with hydrophobic acyl chains was calculated by $^1$H-NMR using a $D_2O$/dioxane mixture as a solvent, according to procedures well known in the art of NMR. The peak area from the ε-methylene group of PLL at 3.0 ppm was compared to that of the methyl group of stearyl-modified poly(L-lysine) at 0.8 ppm. The percent of substitution was calculated from the following equation:

$$\% \text{ substitution} = \frac{(\text{peak area at 0.8 ppm})/3}{(\text{peak area at 3.0 ppm})/2} \times 100$$

It has been discovered that stearyl-PLL having about 18 mole % to about 25 mole % of stearyl groups is preferred for obtaining efficient delivery of nucleic acid into host cells. When the percent of substitution is increased much above about 25 mole %, there is an increase in cytotoxicity of cells treated with the complex. This cytotoxicity is believed due to an increased amount of membrane disruption from the alkyl group bonded to the hydrophobized polymer. When the percent of substitution is decreased much below 18 mole %, there is a decrease in the amount of uptake of the complex by cells, and hence a decrease in the efficiency of delivery.

EXAMPLE 2

Figure 2A:
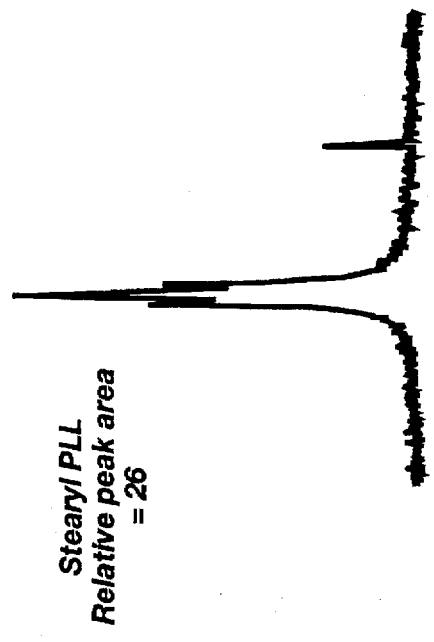
FIGS. 2A–2D show, respectively, proton signals generated by $^1$H-NMR due to the ε-methylene group in (A) stearyl-poly(L-lysine) (stearyl-PLL), (B) a mixture of stearyl-PLL and human low density lipoprotein (LDL), (C) poly(L-lysine) (PLL), (D) a mixture of PLL and LDL.
Figure 2B:
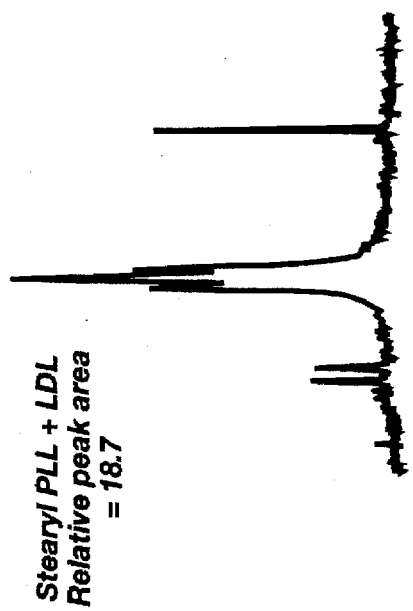
Figure 2C:
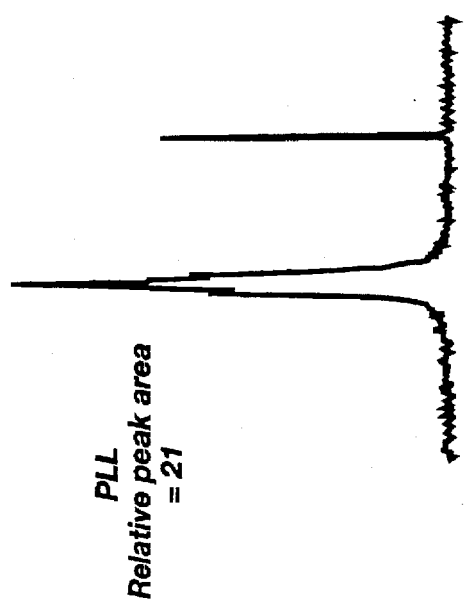
Figure 2D:
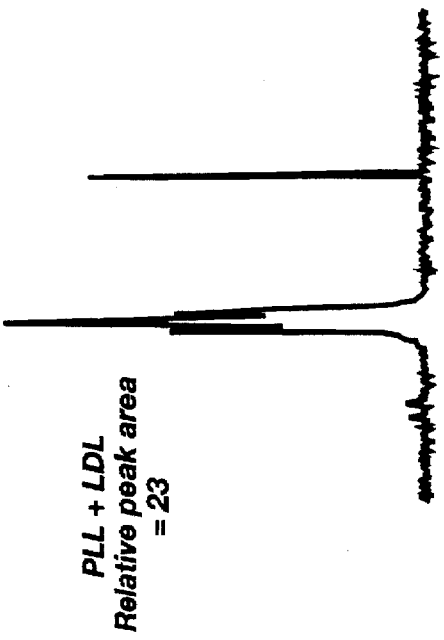

In this example, PLL, stearyl-PLL, a mixture of PLL and human low density lipoprotein (LDL), and a mixture of stearyl-PLL and LDL were separately analyzed by $_1$H-NMR. The results of these analyses are shown in FIGS. 2A–D. The relative peak area or area under the curve (AUC) from the proton signals due to the ε-methylene group in stearyl-PLL (FIG. 2A, 26 AUC units) was 35% greater than the corresponding relative peak area of the mixture of stearyl-PLL and LDL (FIG. 2B, 18.7 AUC units). Unmodified PLL (FIG. 2C, 21 AUC units), which lacks the hydrophobic stearyl group, did not show a significant difference, however, as compared to a mixture of PLL and LDL (FIG. 2D, 23 AUC units). Therefore, the acyl chains in both the stearyl-PLL and the LDL appear to play an important role in a hydrophobic interaction between these two components in a mixture thereof, which results in the reduction in the peak area of the ε-methylene group of the stearyl-PLL when complexed with LDL as compared to the corresponding peak area of stearyl-PLL alone.

EXAMPLE 3

In this example, a gene delivery composition according to the present invention was prepared by mixing stearyl-poly (L-lysine) (stearyl-PLL), human low density lipoprotein (LDL), and pSV-β-gal plasmid DNA (e.g. Promega, Madison, Wis.) or a c-myb antisense oligonucleotide (SEQ ID NO:1) in PBS buffer. Control compositions contained PLL instead of stearyl-PLL. Optical density at 600 nm was measured spectrophotometrically to measure turbidity resulting from aggregation or precipitation of the components. No precipitation or aggregation was observed at wide concentration ranges of stearyl-PLL, LDL, and DNA in PBS. In control compositions containing PLL in place of stearyl-PLL, however, aggregation and/or precipitation was observed. Thus, a stable complex was formed with stearyl-PLL, LDL, and an aqueous DNA solution, whereas compositions containing unmodified PLL instead of stearyl-PLL were unstable as determined by turbidity measurements. It is believed that the hydrophobic interactions between the stearyl-PLL and LDL are responsible at least in part for the formation of the stable DNA-containing complex.

EXAMPLE 4

Figure 3:
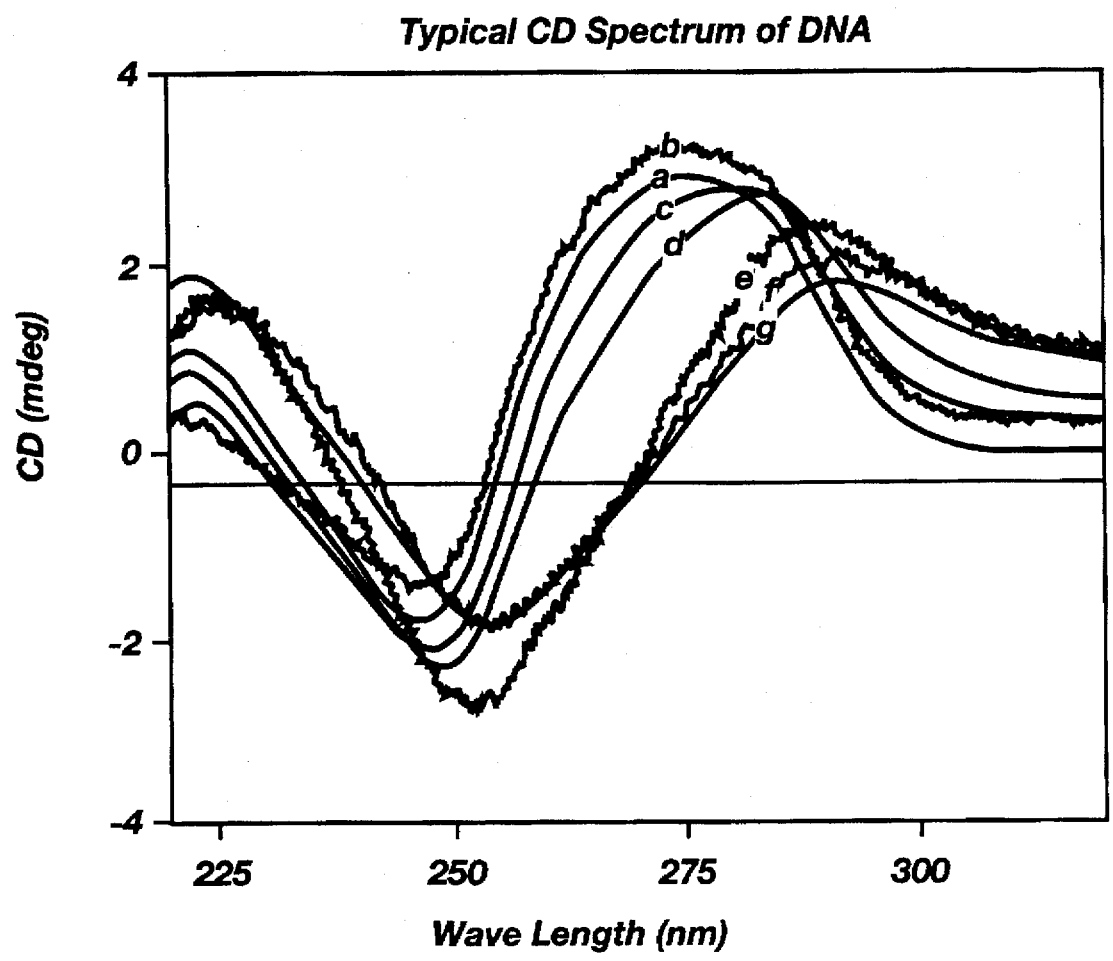
FIG. 3 shows circular dichroism spectra of: (a) pSV-β-gal plasmid DNA; (b) pSV-β-gal plasmid DNA+LDL; (c) pSV-β-gal plasmid DNA+LDL+stearyl-PLL, 1:1:1 by weight; (d) pSV-β-gal plasmid DNA+LDL+stearyl-PLL, 1:1:2 by weight; (e) pSV-β-gal plasmid DNA+LDL+stearyl-PLL, 1:1:3 by weight; (f) pSV-β-gal plasmid DNA+LDL+stearyl-PLL, 1:1:4 by weight; (g) pSV-β-gal plasmid DNA+LDL+stearyl-PLL, 1:1:5 by weight.

Gene delivery complexes prepared with pSV-β-gal plasmid DNA according to the procedure of Example 3 were examined by circular dichroism (CD) analysis with respect to conformational change of the plasmid DNA after complex formation. FIG. 3 shows that the CD spectra of plasmid DNA remained unchanged even though a slight shift in both negative and positive bands at 245 nm and 275 nm, respectively, were observed with the addition of excess stearyl-PLL to the system, e.g. spectra e-g of FIG. 3. Denatured control DNA, on the other hand, resulted in both of these bands being diminished significantly. The shift in bands at 245 nm and 275 nm was not seen when the DNA was treated with a high concentration of salt or with high temperature, suggesting that the plasmid DNA was in a compact configuration rather than denatured in the stearyl-PLL/LDL/plasmid composition.

EXAMPLE 5

In this example, a gene delivery composition comprising stearyl-PLL, LDL, and pSV-β-gal prepared according to Example 3 in a weight ratio of 1:1:1 was used to examine in vitro delivery and expression of the lacZ gene in a murine smooth muscle cell line, A7R5 (ATCC accession no. CRL1444). The plasmid pSV-β-gal (EMBL accession no. X65335) is a positive control vector for monitoring transfection efficiencies of mammalian cells. The pSV-β-gal plasmid comprises an SV40 early promoter and enhancer sequence, transcription start sites, the $E.\ coli$ lacZ coding region encoding β-galactosidase, and the SV40 small T antigen polyadenylation signals. The SV40 early promoter and enhancer drives transcription of the lacZ gene. Cell extracts of transfected cells can be measured directly and easily for β-galactosidase activity with a spectrophotometric assay.

In vitro transfection of the A7R5 cells was performed in 96-well multiwell plates seeded at a cell density of $4 \times 10^4$ cells/ml 24 hours prior to addition of the transfection composition. The stearyl-PLL/LDL/pSV-β-gal composition (10 μl) was added to cells either in the presence or absence of 10% fetal bovine serum. "Serum-free" transfection mixtures were incubated for 4 hours, followed by supplementation with fetal bovine serum to a level of 10%. Cells were incubated for 48 hours in an incubator at 37° C. in 5% $CO_2$, and then the cells were lysed by addition of Promega Reporter Lysis Buffer (cat. no. E3971). The colorigenic indicator O-nitrophenyl-β-D-galactopyranoside (ONPG; Sigma Chemical Co., St. Louis, Mo.) was added to the lysates and incubated an additional 4 hours, and then the $OD_{407}$ was determined as a measure of β-galactosidase activity in the transfected cell lysates. J. H. Miller, Experiments in Molecular Genetics (1972); C. V. Hall et al., 2 J. Mol. Appl. Genet. 101 (1983); P. Norton & J. M. Coffin, 5 Mol. Cell. Biol. 281 (1985). Control transfection experiments were done with cationic liposomes (LIPOFECTIN; Gibco BRL) in a 1:1 weight ratio of liposomes to DNA according to the protocol of the supplier. Additional control formulations were PLL/LDL/pSV-β-gal in a weight ratio of 1:1:1 and stearyl-PLL/pSV-β-gal in a weight ratio of 1:1. Transfections were also done in the presence or absence of 100 μM chloroquine ($NH_4Cl$), a lysosomotropic agent, added 30 min prior to addition of the DNA complex.

Figure 4:
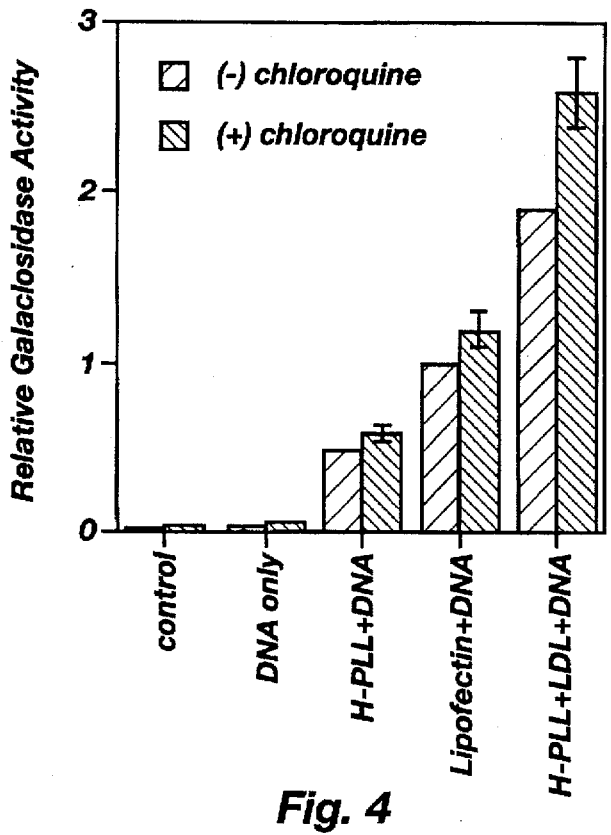
FIG. 4 shows β-galactosidase activity of lysates of A7R5 smooth muscle cells transformed with a lac$^+$ plasmid (pSV-β-gal) according to the present invention: control–no DNA; DNA only–no hydrophobized polymer or lipoprotein; H-PLL+DNA–a complex of hydrophobized poly(L-lysine) and DNA; LIPOFECTIN+DNA–a mixture of cationic polysomes and DNA; H-PLL+LDL+DNA–a complex according to the present invention comprising hydrophobized poly(L-lysine), lipoprotein (human low density lipoprotein) and DNA (pSV-β-gal).

FIG. 4 shows the relative β-galactosidase activity of the composition according to the present invention as compared to various controls. The transfection efficiency, as measured by β-galactosidase activity of transfected cell extracts, was 2-fold higher with the stearyl-PLL/LDL/plasmid composition as compared to the commercially available cationic lipid formulation LIPOFECTIN. The transfection efficiency of the present composition was not affected by the presence of 10% fetal bovine serum, while the efficiency of LIPOFECTIN was decreased by the presence of serum. This result suggests the present composition complexes the DNA such that the DNA is protected from degradation due to nucleases in the serum. Transfection efficiency was increased when lysosomotropic agents such as chloroquine (FIG. 4) or monensin (not shown) were used to pretreat the cells prior to transfection. Cytotoxicity due to the stearyl-PLL/LDL/plasmid composition was not observed.

EXAMPLE 6

The procedure of Example 5 was followed except that compositions having differing surface charges were used to transform the A7S5 cells. Zeta-potential, i.e. the net surface charge, of the DNA-containing complexes was determined at room temperature using a Malvern Zeta-Sizer 3. Conditions for taking these measurements were viscosity of 0.933 and cross beam mode. All of the DNA samples were prepared in PBS. A slightly positive surface charge (about +2-15 mV) provided the highest transfection efficiency with pSV-β-gal without yielding a significant cytotoxicity problem. An especially preferred surface charge was about +5 mV. With a higher positive charge, higher transfection efficiencies could be obtained, but there was also a simultaneous increase in cytotoxicity. Since cells typically have a negatively charged cell surface, it is believed that the positively charged complexes are attracted by electrostatic interactions to the negatively charged cell surface.

Theoretically, the net surface charge of a complex can be predicted by knowing the charges of the components that comprise the complex. In practice, a complex according to the present invention is obtained by mixing the hydrophobized, positively charged, biocompatible polymer; the lipoprotein; and the nucleic acid is selected weight ratios. The net surface charge is then measured by determining the zeta potential. The net surface charge can then be adjusted, if necessary, to achieve a selected net surface charge by adding more negatively charged nucleic acid or more positively charged hydrophobized polymer.

EXAMPLE 7

The procedure of Example 5 was followed except that the size of stearyl-PLL/LDL/plasmid compositions was determined by dynamic laser light scattering (Brookhaven BI-DS) at a 90° angle prior to transfection. Data were analyzed by non-negatively constrained least square analysis. The results of this experiment showed that complexes having an average diameter of about 200 nm resulted in a higher transfection efficiency than complexes having an average diameter of about 400 nm, although such larger complexes were operative for delivery. Preferably, complexes have an average diameter of about 200–400 nm, and more preferably have an average diameter of about 200–300 nm. Notwithstanding this observation, a method of making complexes of a selected average diameter has not yet been developed.

EXAMPLE 8

In this example, the procedure of Example 5 was followed except that c-myb antisense oligonucleotide (SEQ ID NO:1) was substituted for pSV-β-gal and that transfection efficiency was monitored by antiproliferation of A7S5 cells. It has been shown that the c-myb antisense oligonucleotide inhibits proliferation of smooth muscle cells in vitro. M. Simons & R. D. Rosenberg, 70 Cir. Res. 835 (1992). Cells were seeded at a density of $4 \times 10^4$ per well in a 96-well plate 24 hours prior to addition of the oligonucleotide complex, and 24 hours later 10 µl of oligonucleotide complex containing different amounts (µg/well) of c-myb antisense oligonucleotide were added to the cells. Such oligonucleotides can be purchased commercially or can be synthesized by methods well known in the art, e.g. R. B. Merrifield, Solid Phase Peptide Synthesis, 85 J. Am. Chem. Soc. 2149–2156 (1963); R. B. Merrifield et al., 21 Biochemistry 5020-31 (1982); Houghten, 82 Proc. Nat'l Acad. Sci. USA 5131-35 (1985); Hunkapiller et al., 310 Nature 105-111 (1984). The cells were then incubated for 48 hours at 37° C. in 5% $CO_2$ in the presence or absence of 10% fetal bovine serum or 100 µM chloroquine added 30 minutes prior to addition of the DNA complex. The percentage of live cells was determined by MTT colorimetric assay, T. Mosman, 65 J. Immunol. Methods 55 (1983), hereby incorporated by reference. MTT solution (Sigma Chemical Co., St. Louis, Mo.) was added to a final concentration of 50 mg/ml to each well and the cells were incubated an additional 4 hours. The formazan crystal formed in each well was dissolved by addition of 150 µl of DMSO to each well, and the absorbance was measured at 570 nm. The cell proliferation, or % growth, was calculated from the following equation:

$$\% \text{ Growth} = \frac{A_{570(sample)}}{A_{570(control)}} \times 100$$

Figure 5:
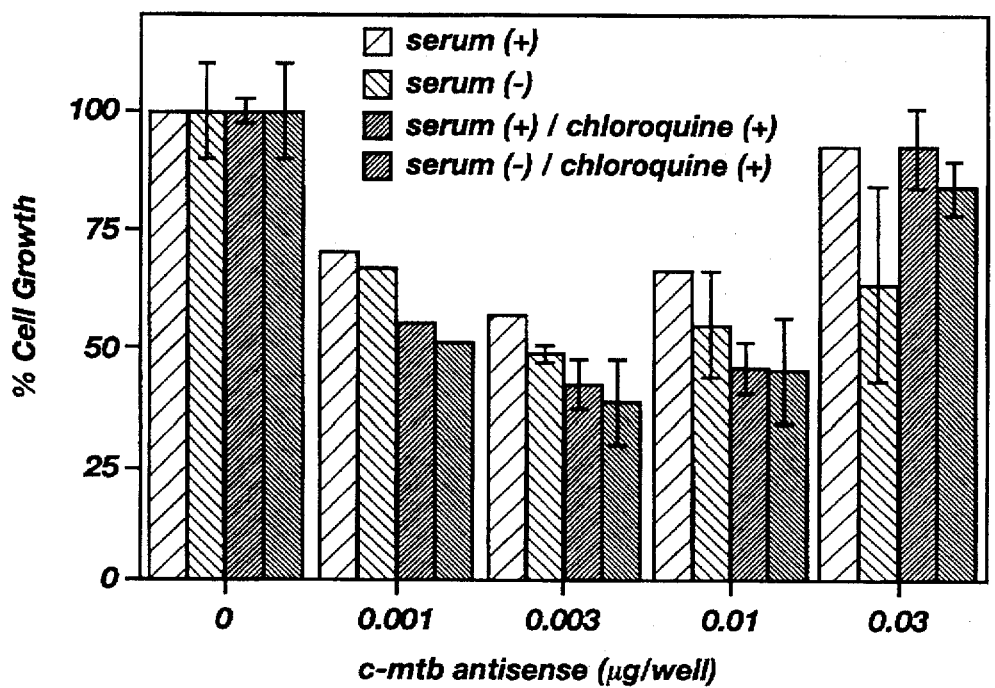
FIG. 5 shows the antiproliferative effect of transformation of A7R5 smooth muscle cells with different amounts of a c-myb antisense oligonucleotide (SEQ ID NO:1) in the presence or absence of 10% fetal bovine serum and 100 μM chloroquine.

FIG. 5 shows that the stearyl-PLL/LDL/oligonucleotide composition resulted in a 50% growth inhibition of smooth muscle cells at a 5 nM concentration of oligonucleotide in the presence of 10% fetal bovine serum. A weight ratio of stearyl-PLL/LDL/oligonucleotide of 1:1:0.006 resulted in the highest inhibitory effect.

EXAMPLE 10

In this example, flow cytometric analysis to investigate internalization of a DNA complex according to the present invention into A7R5 cells was carried out. The complex was labeled with either ethidium-bromide-labeled DNA or BIODIPY-labeled LDL (Molecular Probe, cat. no. L-3483). Cells ($4 \times 10^4$ per well) in a 24-well plate were washed twice with PBS, and then fresh growth medium (DMEM) supplemented with 0.1% bovine serum albumin. The cells were then incubated with a 1:1:1 weight ratio of a stearyl-PLL/LDL/pSV-β-gal complex containing either fluorescence labeled DNA or LDL for 3 hours at 37° C. After washing with PBS three times, the cells were then harvested with trypsin-EDTA and measured for fluorescence intensity (excitation 488 nm and emission 594 nm) using a FACscan™ flow cytometer.

This analysis showed that internalization of the DNA complex into A7R5 cells requires both LDL and divalent cations such as $Mg^{2+}$ or $Ca^{2+}$. The cellular uptake was negligible when a lipoprotein-deficient DNA complex was used. Also, the cellular uptake was decreased by pretreatment with 100 µM EDTA. EDTA is known to deplete the available divalent ions known to be necessary for endocytosis of LDL. J. Goldstein et al., International Cell Biology 639 (Rockefeller Univ. Press, 1977). These findings suggest that internalization is mediated by receptor-mediated endocytosis, presumably by LDL receptors.

---

We claim:

1. A composition for delivery of a selected nucleic acid into a targeted host cell comprising a complex comprising an effective amount of a hydrophobized, positively charged, biocompatible polymer; an effective amount of a lipoprotein; and an effective amount of said selected nucleic acid.

2. The composition of claim 1 wherein said hydrophobized polymer comprises a positively charged biocompatible polymer covalently coupled to a hydrophobic carbon chain moiety.

3. The composition of claim 2 wherein said positively charged biocompatible polymer is poly(L-lysine).

4. The composition of claim 3 wherein said hydrophobic carbon chain moiety is a member selected from the group consisting of saturated and unsaturated, straight-chains of $C_{14}$ to $C_{18}$.

5. The composition of claim 4 wherein said hydrophobic carbon chain moiety is a stearyl group.

6. The composition of claim 3 wherein said lipoprotein is selected from the group consisting of low density lipoprotein, high density lipoprotein, and very low density lipoprotein.

7. The composition of claim 6 wherein said lipoprotein is low density lipoprotein.

8. The composition of claim 7 wherein said selected nucleic acid is a plasmid.

9. The composition of claim 8 wherein said complex comprises about 1 part by weight of stearyl-poly(L-lysine), about 1 part by weight of low density lipoprotein, and about 1 part by weight of said plasmid.

10. The composition of claim 7 wherein said selected nucleic acid is an oligonucleotide.

11. The composition of claim 10 wherein said complex comprises about 1 part by weight of stearyl-poly(L-lysine), about 1 part by weight of low density lipoprotein, and about 0.001–0.05 part by weight of said oligonucleotide.

12. The composition of claim 1 further comprising an effective amount of divalent cations selected from the group consisting of $Ca^{2+}$ and $Mg^{2+}$ and mixtures thereof.

13. The composition of claim 1 wherein said composition has a surface charge in the range of about +2–15 mV.

14. The composition of claim 13 wherein said composition has a surface charge of about +5 mV.

15. The composition of claim 1 wherein said composition has an average diameter in the range of about 200 to 400 nm.

16. The composition of claim 15 wherein said composition has an average diameter of about 200 to 300 nm.

17. A method of transforming a cell in vitro with a selected nucleic acid comprising the steps of:

(a) providing a composition comprising a complex comprising an effective amount of a hydrophobized, positively charged, biocompatible polymer; an effective amount of a lipoprotein; and an effective amount of said selected nucleic acid;

(b) contacting said cell with an effective amount of said composition such that said cell internalizes said selected nucleic acid; and (c) culturing said cell with said internalized selected nucleic acid under conditions favorable for growth of said cell.

18. The method of claim 17 wherein said hydrophobized polymer comprises a positively charged biocompatible polymer covalently coupled to a hydrophobic carbon chain moiety.

19. The method of claim 18 wherein said positively charged biocompatible polymer is poly(L-lysine).

20. The method of claim 19 wherein said hydrophobic carbon chain moiety is a member selected from the group consisting of saturated and unsaturated, straight-chains of $C_{14}$ to $C_{18}$.

21. The method of claim 20 wherein said hydrophobic carbon chain moiety is a stearyl group.

22. The method of claim 20 wherein said lipoprotein is selected from the group consisting of low density lipoprotein, high density lipoprotein, and very low density lipoprotein.

23. The method of claim 22 wherein said lipoprotein is low density lipoprotein.

24. The method of claim 23 wherein said selected nucleic acid is a plasmid.

25. The method of claim 24 wherein said complex comprises about 1 part by weight of stearyl-poly(L-lysine), about 1 part by weight of low density lipoprotein, and about 1 part by weight of said plasmid.

26. The method of claim 23 wherein said selected nucleic acid is an oligonucleotide.

27. The method of claim 26 wherein said complex comprises about 1 part by weight of stearyl-poly(L-lysine), about 1 part by weight of low density lipoprotein, and about 0.001–0.05 part by weight of said oligonucleotide.

28. The method of claim 17 further comprising an effective amount of divalent cations selected from the group consisting of $Ca^{2+}$ and $Mg^{2+}$ and mixtures thereof.

29. The method of claim 17 wherein said composition has a surface charge in the range of about +2–15 mV.

30. The method of claim 29 wherein said composition has a surface charge of about +5 mV.

31. The method of claim 17 wherein said composition has an average diameter in the range of about 200 to 400 nm.

32. The method of claim 31 wherein said composition has an average diameter of about 200 to 300 nm.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

```
         (  i  ) SEQUENCE CHARACTERISTICS:
              ( A ) LENGTH: 18 base pairs
              ( B ) TYPE: nucleic acid
              ( C ) STRANDEDNESS: single
              ( D ) TOPOLOGY: linear ( x i ) SEQUENCE DESCRIPTION: SEQ ID NO:1:

GTGTCGGGGT CTCCGGGC                                      18
```